US011339110B2

(12) United States Patent
Wei et al.

(10) Patent No.: US 11,339,110 B2
(45) Date of Patent: May 24, 2022

(54) EFFICIENT CRYSTALLIZATION PROCESS FOR PREPARING ULTRAPURE TREPROSTINIL AND CRYSTAL PREPARED THEREFROM

(71) Applicant: CHIROGATE INTERNATIONAL INC., Yangmei (TW)

(72) Inventors: Shih-Yi Wei, Yangmei (TW); Jian-Bang Jheng, Yangmei (TW); Ming-Kun Hsu, Yangmei (TW); Min-Kuan Hsu, Yangmei (TW); Tzyh-Mann Wei, Yangmei (TW)

(73) Assignee: CHIROGATE INTERNATIONAL INC., Yangmei (TW)

( * ) Notice: Subject to any disclaimer, the term of this patent is extended or adjusted under 35 U.S.C. 154(b) by 167 days.

(21) Appl. No.: 16/720,711

(22) Filed: Dec. 19, 2019

(65) Prior Publication Data

US 2021/0188757 A1    Jun. 24, 2021

(51) Int. Cl.
*C07C 59/72* (2006.01)
*C07C 51/43* (2006.01)

(52) U.S. Cl.
CPC .............. *C07C 59/72* (2013.01); *C07C 51/43* (2013.01); *C07B 2200/13* (2013.01); *C07C 2603/14* (2017.05)

(58) Field of Classification Search
CPC ..... C07C 59/72; C07C 51/43; C07C 2603/14; C07C 59/125; C07C 51/50; C07C 2603/12; C07B 2200/01; A61P 9/12
See application file for complete search history.

(56) References Cited

U.S. PATENT DOCUMENTS 9,278,903 B2 *  3/2016  Tang .................. C07C 59/72

OTHER PUBLICATIONS

European Search Report dated Apr. 19, 2021.

* cited by examiner

*Primary Examiner* — Deborah D Carr
(74) *Attorney, Agent, or Firm* — Ladas & Parry LLP (57) ABSTRACT

There is provided a crystalline Form I of anhydrous Treprostinil and processes for the preparation thereof. The crystalline Form I of anhydrous Treprostnil is a stable crystalline form, which can provide steady physicochemical properties for pharmaceutical formulations, and is advantageous widely and safety used in storage, shipment, and handling for commercially considerations.

16 Claims, 11 Drawing Sheets

EFFICIENT CRYSTALLIZATION PROCESS FOR PREPARING ULTRAPURE TREPROSTINIL AND CRYSTAL PREPARED THEREFROM

FIELD OF THE INVENTION

The present invention relates to an efficient crystallization process for preparing ultrapure Treprostinil and also relates to a novel crystalline form of anhydrous Treprostinil prepared therefrom.

BACKGROUND OF THE INVENTION

Treprostinil (UT15) is a synthetic analogue of benzoprostacyclin having the following structural formula.

Treprostinil (UT15)

Treprostinil is used for pulmonary arterial hypertension (PAH) patient to improve the exercise capacity. Depending on the route of administration, the medicament can be prepared into various dosage forms, e.g., injection, oral, inhalation, etc. US2015/148414 revealed that the infused Tyvaso® (Treprostinil) is a long acting pulmonary vasodilator providing significantly lower plasma levels for treating pulmonary hypertension. Remodulin® (treprostinil sodium) Injection is another formulation approved by U.S. Food and Drug Administration (FDA) for treating PAH, which is a sterile sodium salt formulated for subcutaneous or intravenous administration. WO 2016/038532 discloses that the amorphous solid dispersions of Treprostinil diethanolamine may be used in the formulation of tablets for oral administration. U.S. Pat. Nos. 6,521,212 and 6,756,033 also disclose the treatment of pulmonary hypertension by inhalation of Treprostinil.

Treprostinil is a high polarity compound containing one carboxylic acid (—COOH) and two hydroxyl (—OH) functional groups, which is very difficult to be purified by silica gel column chromatography. Therefore, the most feasible way for Treprostinil purification in industry is crystallization.

The current regulations require that each impurity in active pharmaceutical ingredients should be present in an amount of less than 0.1%. For drug safety, it is expected in industry that the purification efficiency of a crystallization process can increase the purity of Treprostinil to 99.95% or above, so as to ensure that the amount of each single impurity is less than 0.1%. However, in the prior art, there are only few references regarding the crystals and purification of Treprostinil, and none of them can successfully increase the purity of Treprostinil to 99.95% or above, even after a repetition of the crystallization process is performed. The reasons are as follows.

Reason 1: Esterification impurities would be generated during the crystallization of Treprostinil.

According to the following Example 1, when dissolving Treprostinil in ethanol for crystallization, Treprostinil ethyl ester will be generated at an hourly rate of about 0.2% at about 40° C.; and when storing almost pure Treprostinil at an environment of about 40° C., Treprostinil dimers will be generated at an hourly rate of about 0.01%. The experimental results show that the —COOH functional group in Treprostinil is very active, so Treprostinil is easily esterified with alcohols including Treprostinil itself to form esters or dimers thereof.

J. Org. Chem. 69, 1890-1902 (2004) discloses that the purity of Treprostinil synthesized by a crystallization process in an ethanol-water system is only 99.7%. The reference does not further analyze the 0.3% impurities. Nevertheless, according to the above experimental results, it can be reasonably deduced that most of the 0.3% impurities are Treprostinil ethyl ester. Thus, even such a crystallization process is performed repeatedly many times, it cannot be guaranteed that the purity of Treprostinil can be increased to 99.95% or above.

WO 2009/137066 also discloses the preparation of Treprostinil monohydrate and anhydrous Treprostinil by crystallization in an ethanol-water system. According to the experimental results of Lot No. D-1007-089 and Lot No. 1M07033, the synthesized Treprostinil monohydrates comprise 0.2% Treprostinil Ethyl Ester or UT-15 Ethyl Ester, and 0.13% to 0.14% Treprostinil dimers (i.e., 750W93+751W93). In particular, the anhydrous Treprostinil of Lot No. 01A07002 contains 0.5% Treprostinil dimers (0.2% 750W93+0.3% 751W93). These dimers may be generated during the high-temperature drying procedure.

U.S. Pat. Nos. 9,278,902 and 9,278,903 disclose the crystallization of Treprostinil by using solvents other than ethanol, so as to avoid generating Treprostinil ethyl ester. However, since the current regulations also include very strict requirements with regard to the residual amount of the non-ethanol solvents, the time for removing the residual solvents by using high-temperature drying would be significantly increased and also the opportunities of producing dimers. Moreover, all of the working examples of U.S. Pat. Nos. 9,278,902 and 9,278,903 illustrate the synthesis of only about 1 g crystallized products with an average HPLC purity of about 99.70%, and the highest of only 99.90%, which is still less than 99.95% as required. When mass production is needed, it is difficult to expect that the HPLC purity of the product can still reach 99.90%, even 99.95% or above.

Reason 2: Treprostinils disclosed in the prior art references are all gummy solids or viscous substances, and thus are difficult to be filtered and dried.

WO 2009/137066, U.S. Pat. Nos. 9,278,902, and 9,278,903 disclose that the crude Treprostinil obtained by extracting the reaction solution with ethyl acetate and concentrating is a slightly yellow gummy solid. U.S. Pat. Nos. 9,278,902 and 9,278,903 disclose that the Treprostinil monohydrate obtained by using an ethanol-water system is an extremely viscous substance. US 2014/275262 discloses two crystalline Treprostinil monohydrate Form A and Form B, which are in the form as a slurry and difficult to be filtered. Therefore, it can be seen that whether Treprostinils or Treprostinil monohydrates are essentially viscous substances, which are difficult to be filtered or cleaned. Since the products are difficult to be filtered, it is unable to estimate how long the filtration time is required or how much the esterification impurities would be produced.

In view of the above, to obtain ultrapure Treprostinil (>99.95%) with any single impurity of less than about 0.1% and solve all the problems with respect to the crystallization process of Treprostinil, it is still looking for a more efficient crystallization process for purification in industry.

SUMMARY OF THE INVENTION

Upon research, the inventor found a more efficient crystallization process for preparing anhydrous Treprostinil which has a purity of at least 99.95% aside from the residual solvents and water, and surprisingly found a novel crystalline form of anhydrous Treprostinil, which has low viscosity and thus can be easily removed from the bucket and then filtrated and rinsed due to its compact solid feature. The inventive rapid and efficient crystallization process can completely avoid generating the esterification impurities, and is more suitable for use in mass production in industry.

According to one aspect, the present invention provides a substantially pure crystalline anhydrous Treprostinil Form I, having a X-ray powder diffraction (XRPD) pattern comprising a most strong characteristic peak at 3.1±0.2° and substantially free of characteristic peak at 6.5±0.2°; and having a differential scanning calorimetry (DSC) thermogram pattern comprising a most strong endothermic peak at approximately 124±5° C. and substantially free of endothermic peak at approximately 95±5° C.

In one embodiment, the DSC thermogram pattern of the crystalline anhydrous Treprostinil Form I further comprises a minor endothermic peak having an enthalpy of not more than about 10 J/g, at approximately 60 to 80° C.

According to the other aspect, the present invention provides a crystalline anhydrous Treprostinil containing less than about 0.05% Treprostinil ethyl ester and less than about 0.05% Treprostinil dimers.

In one embodiment, the present invention provides a crystalline anhydrous Treprostinil containing less than 0.02% Treprostinil ethyl ester and less than 0.02% Treprostinil dimers.

In one embodiment, the present invention provides a crystalline anhydrous Treprostinil having a purity of at least 99.95% aside from the residual solvents and water.

According to another aspect, the present invention provides a method for preparing the crystalline anhydrous Treprostinil Form I.

In one embodiment, the present invention provides a substantially pure crystalline Form I of anhydrous Treprostinil having a DSC thermogram pattern comprising only two endothermic peaks, one major endothermic peak having an enthalpy of greater than about 60 J/g, at approximately 124±5° C. and one minor endothermic peak having an enthalpy of not more than about 10 J/g, at approximately 60 to 80° C.

In one embodiment, the present invention provides a substantially pure crystalline Form I of anhydrous Treprostinil having a X-ray powder diffraction (XRPD) pattern comprising a strongest characteristic peak at 3.1±0.2° and substantially free of a characteristic peak at 6.5±0.2° and having a DSC thermogram pattern comprising only two endothermic peaks, one major endothermic peak having an enthalpy of greater than about 60 J/g, at approximately 124±5° C. and one minor endothermic peak having an enthalpy of not more than about 10 J/g, at approximately 60 to 80° C.

DETAILED DESCRIPTION OF THE INVENTION

Preparation of Crystalline Treprostinil

A typical synthesis process of crystalline Treprostinil is shown in the following Scheme A:

Scheme A

Y: —COOR or —CN

Treprostinil

*J. Org. Chem.* 69, 1890-1902 (2004) discloses detailed steps of the above synthesis as follows:
(a) dissolving Treprostinil ester or Treprostinil nitrile in a methanol-water solution;
(b) adding a strong base such as KOH for hydrolysis reaction:
(c) optionally adding an acid such as HCl to adjust the pH value to 10 to 12;
(d) concentrating for removing methanol to form an aqueous solution;
(e) washing the aqueous solution by ethyl acetate;
(f) adjusting the pH value of the residual aqueous solution to 2 to 3 by adding HCl;
(g) extracting by ethyl acetate;
(h) optionally washing the combined organic layers with water;
(i) drying the extraction solution of Treprostinil by adding anhydrous Na2SO4 for removing residual water, and then filtering;
(j) concentrating the dried extraction solution of Treprostinil to obtain the crude Treprostinil as a gummy solid;
(k) heating the gummy solid to dissolve crude Treprostinil into a good solvent such as ethanol to give a homogenous solution;
(l) lowering the temperature and/or adding a poor solvent such as water to precipitate Treprostinil crystals;
(m) filtering;
(n) washing; and
(o) drying.

WO 2009/137066 discloses a process for preparing Treprostinil monohydrate comprising directly dissolving Treprostinil Diethanolamine in water to form an aqueous solution of the above step (e), and performing the same steps (f) to step (o) to obtain Treprostinil crystals. U.S. Pat. Nos. 9,278,902 and 9,278,903 disclose a process comprising the same steps as provided in *J. Org. Chem.* 69, 1890-1902 (2004), but different recrystallization solvents (good solvent and poor solvent) and operation conditions in step (k) to step (o).

The inventor analyzed the above conventional steps in accordance with the stability test results of Example 1 of the present invention and found that the steps that would most likely generate the esterification impurity of Treprostinil ethyl ester may include step (k) of heating and dissolving crude Treprostinil in ethanol, and step (k) to step (o). As long as ethanol is not completely removed, Treprostinil ethyl ester may occur.

Moreover, the steps that would most likely generate the esterification impurity of Treprostinil dimers may be step (j) of concentrating and drying for forming the gummy crude Treprostinil solid, and step (k) of heating and dissolving the gummy crude Treprostinil solid in the good solvent. In step (k), although the surface of the gummy solid will be firstly dissolved in the good solvent and thus dimers are less likely to be formed, the interior of the gummy solid contains high concentration Treprostinil and thus dimers are easily produced. Especially when the above conventional synthesis process is used in mass production in industry, the gummy solid is adhered to the wall of the reaction bucket, and the gummy solid opposite to the wall of the reaction bucket will start to dissolve. However, the heat medium is heating through the wall of the reaction bucket, so if the solvent is desired to heated to about 40° C. to 50° C., the wall temperature of the reaction bucket will be much higher than 50° C. At this time, the gummy Treprostinil adhered to the reaction bucket will convert to a large amount of dimers. Moreover, since the filtration rate in step (m) is difficult to be expect, if the filtration time is too long, dimers would be easily formed. The key step affecting the generation of dimers is the final drying step (o). WO2009/137066 discloses that anhydrous treprostinil will be formed in an ethanol-water system after drying at 55° C. and 0.26 Torr for 22.7 hours. However, such drying conditions would easily result in forming a large amount of dimers. In addition, U.S. Pat. Nos. 9,278,902 and 9,278,903 illustrate the use of aprotic solvents for crystallization. The selection of aprotic solvents will also affect the generation amount of dimers. For example, although solvents with low boiling points and low polarity are evaporated, they would have poor solubility relative to Treprostinil and thus are not suitable for use in crystallization; although solvents with high boiling points and high polarity are more suitable for crystallization, it is not easy to reduce the amounts of the solvents to less than the regulatory limits under vacuum within a short time period, and most cases are even harder to dry than water.

Consequently, in order to avoid generating the esterification impurities, a better strategy is to crystallize in step (i), thereby the re-crystallization steps of step (j) to step (k) can be omitted, and the concentration and drying step (j) can also be neglected. However, the reason why none of the prior art references disclosing the crystallization at step (i) is that a filterable crystal cannot be obtained at step (i). WO 2009/137066 discloses that the crude Treprostinil obtained at step (i) is a gummy solid. U.S. Pat. Nos. 9,278,902 and 9,278,903 also disclose that the crude Treprostinil obtained at step (i) is a slightly yellow gummy solid, and disclose that the reaction liquids are difficult to be filtered and the residual solvent cannot be completely removed under reduced pressure. In view of the above, if the crude Treprostinil can be formed in the format of a filterable crystal, rather than a gummy solid at step (i), many steps that might generate the esterification impurities can be omitted.

The inventor has tried many ways and many times in order to solve the above mentioned problems, and unexpectedly and surprisingly found the following novel aspects of crystalline Treprostinil:
(a) A wet Treprostinil crystal is precipitated from a solution comprising an aprotic solvent and about 1% to about 8% water, which is still a Treprostinil crystal with compact solid feature. The filtered Treprostinil crystal is measured by the Karl Fischer titration immediately. The result shows that the water content is less than 2%, indicating that the wet Treprostinil crystal is Treprostinil rather than Treprostinil monohydrate (containing about 4% water).
(b) The wet Treprostinil crystal in a solution comprising an aprotic solvent and about 1% to about 8% water is more filterable than Treprostinil monohydrate crystal in aprotic-aqueous solvent (WO 2009/137066) and also more filterable than anhydrous Treprostinil crystal in an anhydrous aprotic solvent (U.S. Pat. No. 9,278,903).

Figure 3:
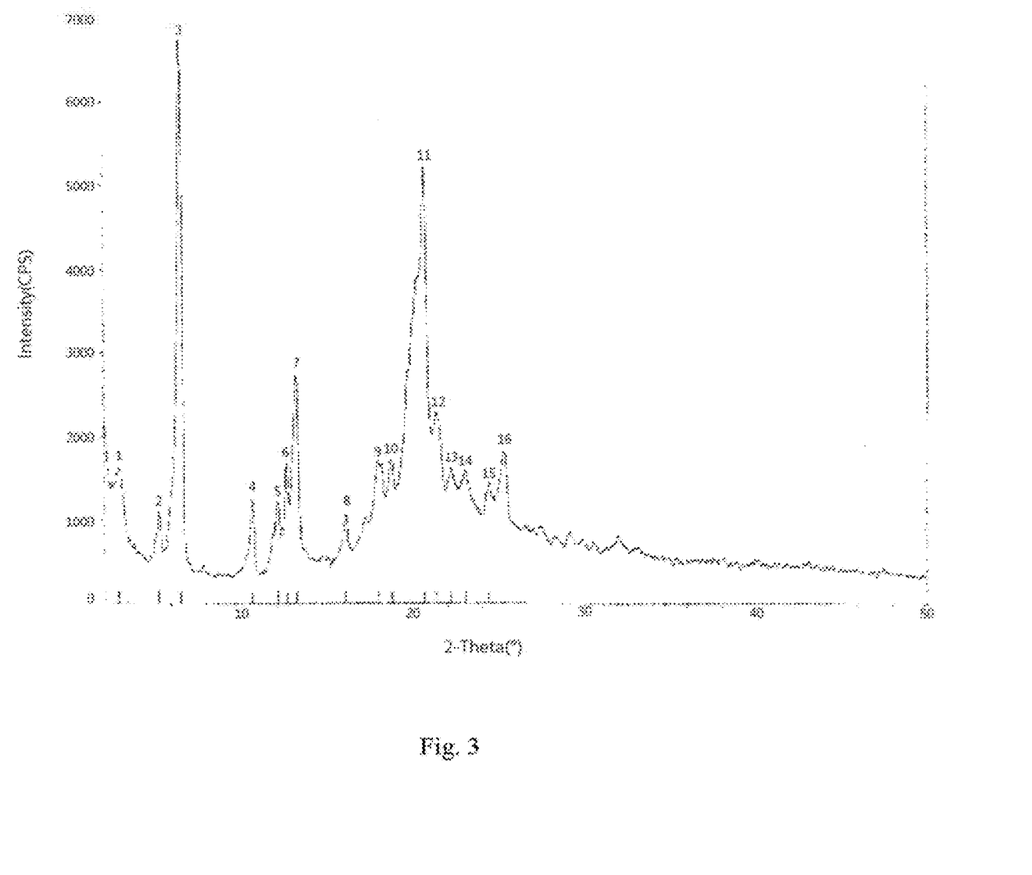
FIG. 3 shows an X-ray powder diffraction (XRPD) pattern of crystalline Form B of anhydrous Treprostinil obtained in Example of U.S. Pat. No. 9,278,902.
Figure 5:
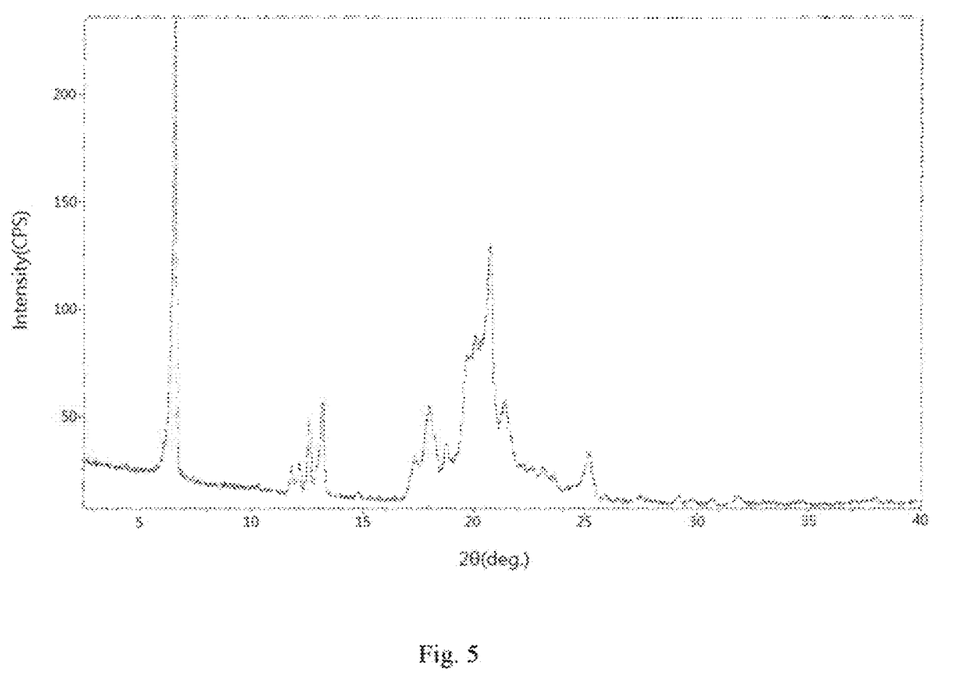
FIG. 5 shows an X-ray power diffraction (XRPD) pattern of crystalline Form C of anhydrous Treprostinil obtained in Example of US 2014/275262.
Figure 7:
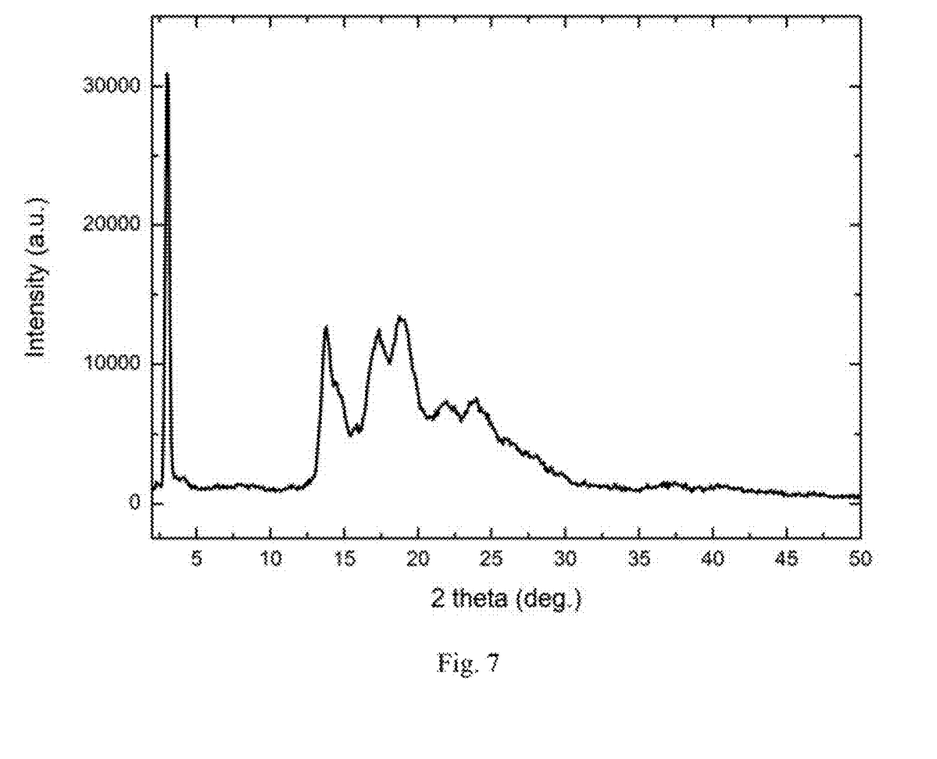
FIG. 7 shows an X-ray power diffraction (XRPD) pattern of the crystalline Form I of anhydrous Treprostinil of the present invention.

(c) After washing and drying the wet Treprostinil crystal, a novel single crystalline anhydrous form of Treprostinil, hereinafter referred to as crystalline anhydrous Treprostinil Form I, or crystalline Form I of anhydrous Treprostinil, or Form I, was obtained. The novel crystalline anhydrous Treprostinil Form I has a X-ray powder diffraction (XRPD) pattern comprising a strongest characteristic peak at 3.1±0.2° and substantially free of characteristic peak at 6.50±0.2°, and having a DSC thermogram pattern comprising a strongest endothermic peak at approximately 124±5° C. and substantially free of endothermic peak at approximately 95±5° C. Compared to the X-ray powder diffraction (XRPD) pattern of known crystalline anhydrous Treprostinil Form A (FIG. 1 of U.S. Pat. No. 9,278,903, reproduced as FIG. 1), Form B (FIG. 1 of U.S. Pat. No. 9,278,902, reproduced as FIG. 3), and Form C (FIG. 16 of US 20141275262, reproduced as FIG. 5), all of the anhydrous Treprostinil crystals show a series of board (FWHH>5°) or multi-split characteristic peaks at the range of 10° to 30°. At the range within 10°, Form A shows a stronger peak at 2.96° (3.1±0.2°) and a weaker peak at 6.52 (6.5±0.2°), Form B shows a weaker peak at 2.90 (3.1±0.2°) and a stronger peak at 6.56 (6.5±0.2°), Form C shows only a stronger peak at 6.55° (6.5±0.2°), but as shown in FIG. 7, Form I of the present invention shows only a stronger peak at 3.1±0.2° and substantially free of characteristic peak at 6.5±0.2°. Form I is clearly different from Form A. Form B, or Form C.

Figure 2:
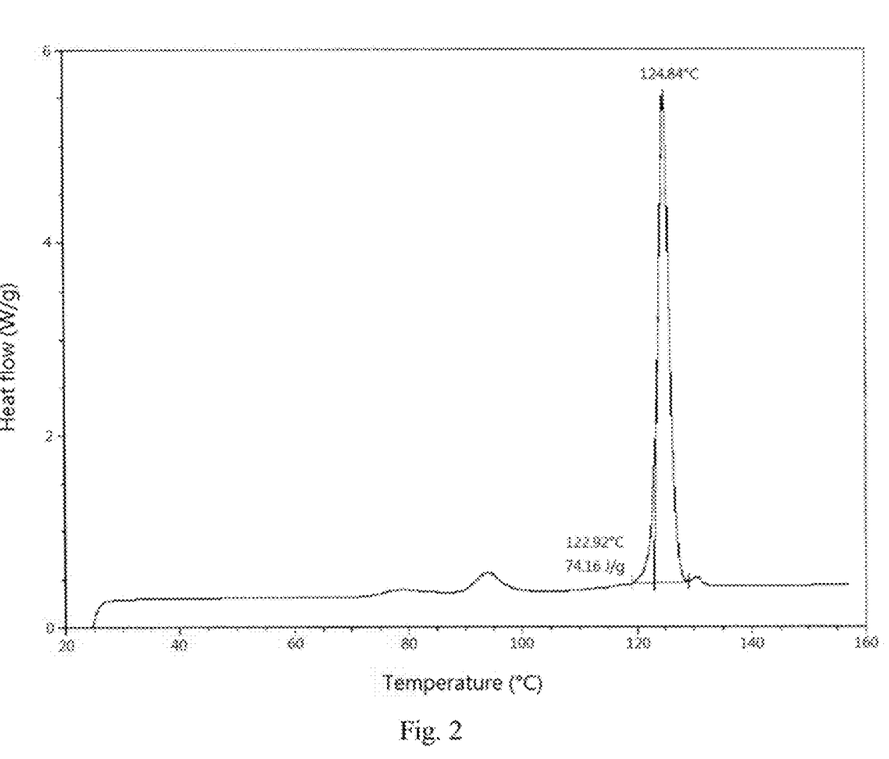
FIG. 2 shows a differential scanning calorimetry (DSC) thermogram pattern of crystalline Form A of anhydrous Treprostinil obtained in Example of U.S. Pat. No. 9,278,903.
Figure 4:
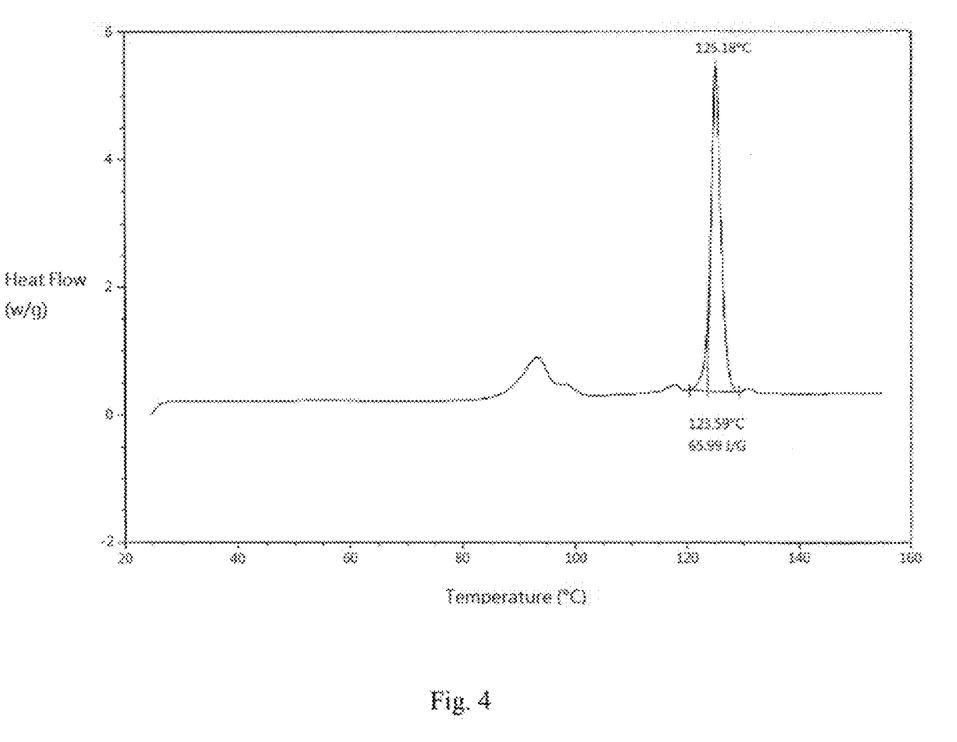
FIG. 4 shows a differential scanning calorimetry (DSC) thermogram pattern of crystalline Form B of anhydrous Treprostinil obtained in Example of U.S. Pat. No. 9,278,902.
Figure 6:
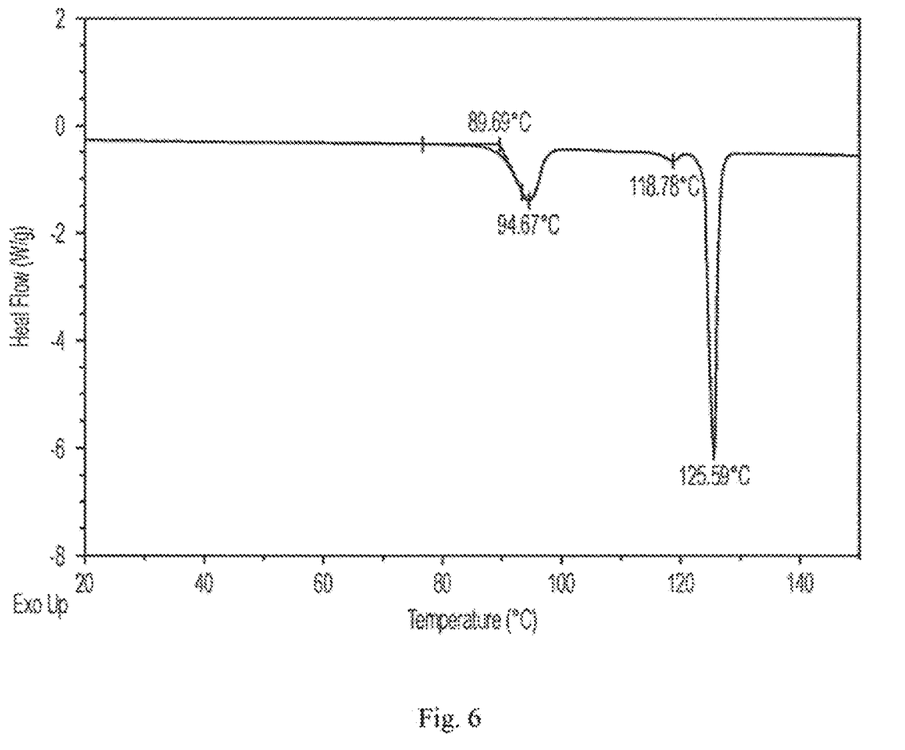
FIG. 6 shows a differential scanning calorimetry (DSC) thermogram pattern of crystalline Form C of anhydrous Treprostinil obtained in Example of US 2014/275262.
Figure 8:
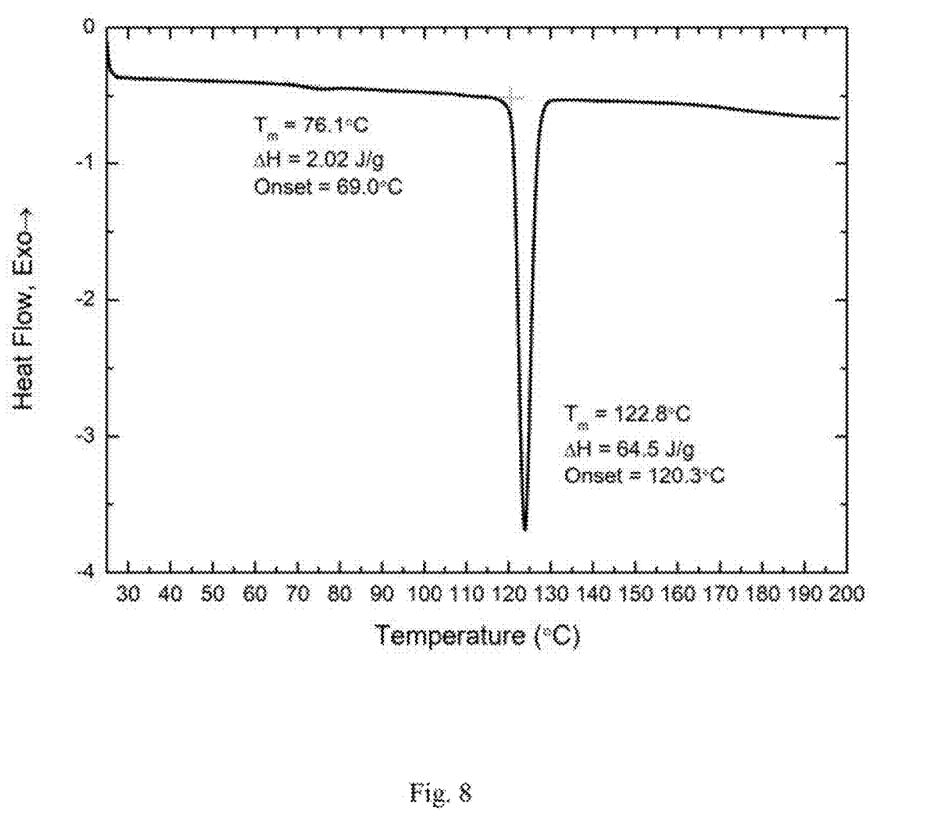
FIG. 8 shows a differential scanning calorimetry (DSC) thermogram pattern of the crystalline Form I of anhydrous Treprostinil of the present invention.

Compared to the DSC thermogram pattern of known crystalline anhydrous Treprostinil Form A (FIG. 2 of U.S. Pat. No. 9,278,903, reproduced as FIG. 2), Form B (FIG. 2 of U.S. Pat. No. 9,278,902, reproduced as FIG. 4), and Form C (FIG. 17 of US 2014/275262, reproduced as FIG. 6). The DSC thermogram patterns of the crystalline Form A, Form B, and Form C of anhydrous Treprostinil all comprise two major endothermic peaks at approximately 95±5° C. and approximately 124±5° C., and obviously two to three other endothermic peaks, as shown in FIG. 2, FIG. 4 and FIG. 6, respectively. However, as shown in FIG. 8, the crystalline Form I of anhydrous Treprostinil of the present invention comprises only a major endothermic peak at approximately 124±5° C. and substantially free of endothermic peak at approximately 95±5° C. Form I is a single crystalline form with high melting point and is clearly different from Form A, Form B, or Form C.

No matter referring to the XRPD pattern or the DSC thermogram pattern, the crystalline Form I of anhydrous Treprostinil is obviously different from conventional crystalline Form A, Form B, and Form C. Therefore, the crystalline Form I of anhydrous Treprostinil is a novel crystalline form. Moreover, the DSC thermogram patterns of the conventional crystalline Form A, Form B, and Form C all comprise three to five endothermic peaks, but the DSC thermogram pattern of the crystalline Form I anhydrous Treprostinil comprises nearly a single endothermic peak, which means that the crystalline Form I of anhydrous Treprostinil is mostly a single pure crystalline form.

(d) The water content of the extraction solution of Treprostinil must range from about 1% to 8% (v/v) for assisting the crystallization of Treprostinil during stirring and concentrating. Since the extraction solution of Treprostinil only contains about 1% to 8% (v/v) water, the step (i) of adding anhydrous $Na_2SO_4$ to the extraction solution of Treprostinil for removing residual water as disclosed by *J. Org. Chem.* 69, 1890-1902, WO 2009/137066, U.S. Pat. Nos. 9,278,902, and 9,278,903 can therefore be omitted. In the present invention, the extraction solution of Treprostinil containing only about 1 to 8% (v/v) water is directly stirred and concentrated at 30±5° C. under vacuum (about 1 to 200 torr)) until most precipitate crystals are formed. Then stop concentrating, and filter out and rinse the precipitated crystals. The precipitated Treprostinil crystals have low viscosity and good filterability.

(e) After washing and drying the wet Treprostinil crystal, the inventor found a novel Treprostinil crystal containing less than about 0.05% Treprostinil ethyl ester and less than about 0.05% Treprostinil dimers, preferably containing less than about 0.02% Treprostinil ethyl ester and less than about 0.02% Treprostinil dimers, more preferably containing less than about 0.01% Treprostinil ethyl ester and less than about 0.01% Treprostinil dimers, and the most preferably containing non-detectable amounts of Treprostinil ethyl ester and Treprostinil dimers. The inventor also found that the novel Treprostinil crystal has a purity more than about 99.90%, preferably more than about 99.95%, and most preferably more than about 99.99%.

The inventor unexpectedly found that if directly concentrating and crystallizing the extraction solution of Treprostinil in the conventional step (h), the obtained ultrapure Treprostinil would meet the strictest requirements of regulations. In such cases, the step (j) that will generate gummy solids and the step (k) and the subsequent steps for recrystallization can be avoided. Most of the steps that may easily form the esterification impurities can be omitted, so as to reduce work hours and save coast. The present invention provides an efficient crystallization process for preparing ultrapure Treprostinil.

Preparation of Ultra Pre Anhydrous Treprostinil and its Crystal

The present invention provides a method for preparing the crystalline Form I of anhydrous Treprostinil containing less than about 0.05% Treprostinil ethyl ester and less than about 0.05% Treprostinil dimers, which comprises the steps of:

(a) providing a Treprostinil solution containing Treprostinil, an organic solvent selected from the group consisting of methyl acetate, ethyl acetate, isopropyl acetate, and mixtures thereof, and about 1% to 8% (v/v) water;

(b) concentrating the Treprostinil solution under vacuum at 30±15° C. until most Treprostinil crystals are precipitated;

(c) filtering out and optionally rinsing the precipitate crystals thereby isolating the Treprostinil crystals; and (d) drying the Treprostinil crystals at 20±5° C.

In the present invention, the volume of the organic solvent may be about 15 ml to about 100 ml, preferably about 15 ml to about 50 ml, and more preferably about 20 ml to about 50 ml, per 1 g of the Treprostinil. The water content (v/v) may be about 1% to about 8%, preferably about 2% to about 6%, and more preferably about 3% to about 5% relative to the organic solvent. The Treprostinil can be dissolved in a solution comprising the organic solvent and about 1% to 8% (v/v) water at a temperature ranging from about 0° C. to about 80° C., preferably from about 10° C. to about 60° C., and more preferably from room temperature to about 40° C.

WO 2009/137066 discloses that the crude Treprostinil was concentrated from the extraction organic layer of reaction after dried by $Na_2SO_4$. In chemical and industrial fields, it is well known that the extraction organic layer of reaction should be treated by stirring with $Na_2SO_4$ to remove residual water before concentrating. However, in the case of Treprostinil as prepared by WO 2009/137066, the concentrated crude Treprostinil was a gummy solid with high viscosity, which might not be easily removed from the bucket, filtrated and rinsed. As an unexpected discovery, the inventor surprisingly found that containing a moderate amount of water in the Treprostinil solution can help the Treprostinil to form a white granular crystal with compact solid characteristic while concentrating. The Treprostinil crystal has low viscosity and can be easily peeled from the bucket, filtrated and rinsed due to its compact solid feature. In one embodiment, the extraction organic layer of reaction without dried by $Na_2SO_4$ as disclosed by J. Org. Chem. 69, 1890-1902, WO 2009/137066, U.S. Pat. Nos. 9,278,902, and 9,278,903 can be used as the Treprostinil solution containing a moderate amount of water of the present invention. In other words, in the present invention, the extraction organic layer without dried by $Na_2SO_4$ can be directly used to crystallize.

Figure 1:
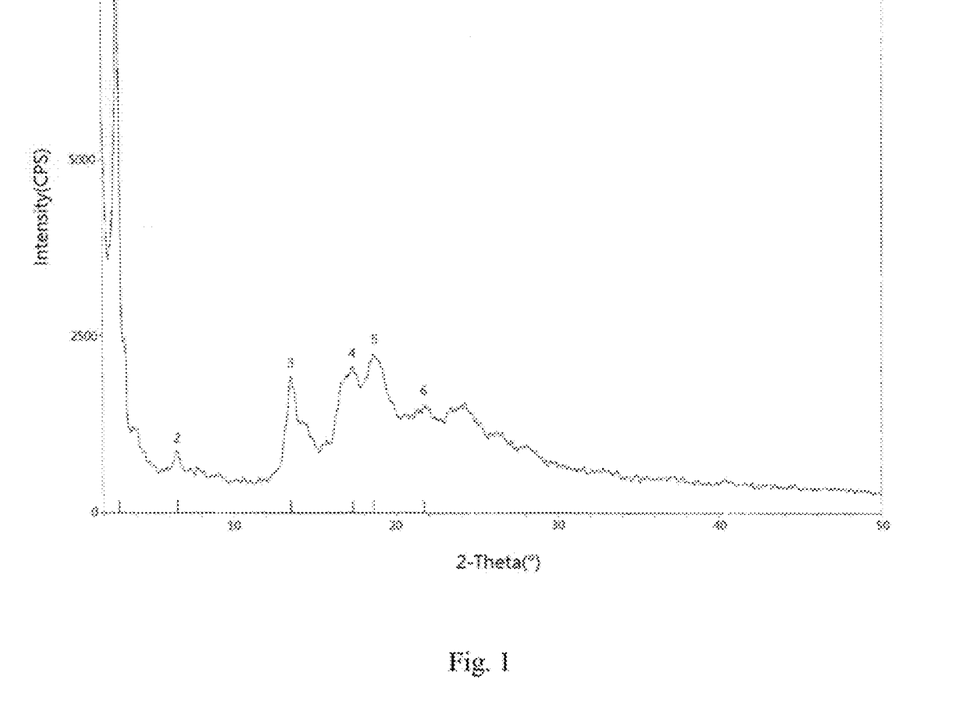
FIG. 1 shows an X-ray powder diffraction (XRPD) pattern of crystalline Form A of anhydrous Treprostinil obtained in Example of U.S. Pat. No. 9,278,903.

Regarding the method of precipitation of Treprostinil crystal, U.S. Pat. No. 9,278,903 discloses the steps of cooling solution 1 comprising crude Treprostinil and one or more solvents such as ethyl acetate but without water and/or adding solvent 2 such as C5-C8 alkane, and cool drown to 0-5° C. to give the crystalline Form A. As shown in all the working examples of U.S. Pat. No. 9,278,903, the obtained crystalline anhydrous Treprostinil Form A has a differential scanning calorimetry (DSC) thermogram pattern comprise an endothermic peak at approximately 95° C. (FIG. 2), and has a X-ray powder diffraction (XRPD) pattern comprising a characteristic peak at 6.5±0.2° (FIG. 1).

In the present invention, Treprostinil is concentrated in an aqueous ethyl acetate solution at normal temperature or upon slightly heating. When an aqueous ethyl acetate solution of Treprostinil is evaporated until the concentration exceeds the saturation level of Treprostinil, filamentous crystals which are not gummy solids but are crystalline Form I of anhydrous Treprostinil will be generated. The DSC thermogram pattern of the crystalline Form I does not have an endothermic peak at approximately 95±5° C., and the XRPD pattern of the crystalline Form I does not have a characteristic peak at 6.5±0.2°.

In the present invention, the concentrating step is performed at a temperature ranging from about 0° C. to about 70° C., preferably from about 10° C. to about 60° C., and more preferably from about 15° C. to about 45° C.

Proper high-temperature concentrating step than U.S. Pat. No. 9,278,903 is an important factor that promotes the crystallization of Treprostinil to form a white granule crystal with compact solid feature, rather than gummy viscous solid. Moreover, the impurities of Treprostinil can be almost dissolved in the proper high-temperature solution, and a high purity Treprostinil crystal can be obtained after filtration.

The concentrating step can be performed under reduced pressure of about 1 Torr to about 200 Torr, preferably about 2 Torr to about 100 Torr, and preferably about 5 torr to about 50 torr.

Due to the using of the specific organic solvent system in the method of the present invention, the precipitated crystalline Form I of anhydrous Treprostinil possesses compact solid feature and good filterability. The residual solvent of anhydrous Treprostinil crystal can be easily removed under high vacuum (preferably about 0.001 to 10 Torr) at room temperature. Moreover, the dried anhydrous Treprostinil crystal with granular and compact solid feature is much easier to weight for commercially handling comparing with the gummy solid form of Treprostinil with high viscosity.

In one embodiment of the present invention, the crystalline Form I of anhydrous Treprostinil is substantially free of any other form of crystalline treprostinil. In one embodiment, the crystalline Form I of anhydrous Treprostinil has an XRPD pattern exhibits a strongest characteristic peak at 3.1±0.2° and substantially free of characteristic peak at 6.5±0.2°. In a preferred embodiment, the XRPD pattern further comprises a series of rough or multi-split characteristic peaks at 13.8±0.2°, 17.5±0.2°, and 18.9±0.2°. More preferably, the XRPD pattern of crystalline Form I of anhydrous Treprostinil is consistent with FIG. 7. The particular XRPD data of crystalline Form I of anhydrous Treprostinil is shown in Table 1.

TABLE 1

| 2θ angle (°) | d value (Å) | relative intensity (%) |
|---|---|---|
| 3.1 | 28.8 | 100.0 |
| 13.8 | 6.4 | 39.5 |
| 17.5 | 5.1 | 38.9 |
| 18.9 | 4.7 | 41.7 |
| 22.0 | 4.0 | 22.9 |
| 23.8 | 3.7 | 23.4 |

In one embodiment, the present invention provides a crystalline Form I of anhydrous Treprostinil having a DSC thermogram pattern comprising a strongest endothermic peak at approximately 124±5° C. and substantially free of endothermic peak at approximately 95±5° C.

In one embodiment, the present invention provides a crystalline Form I of anhydrous Treprostinil having a DSC thermogram pattern further comprising a week endothermic peak, which the enthalpy is not more than 10 J/g, at approximately 60 to 80° C. In a preferred embodiment, the present invention provides a crystalline Form I of anhydrous Treprostinil having a DSC thermogram pattern substantially as shown in FIG. 8.

Figure 9:
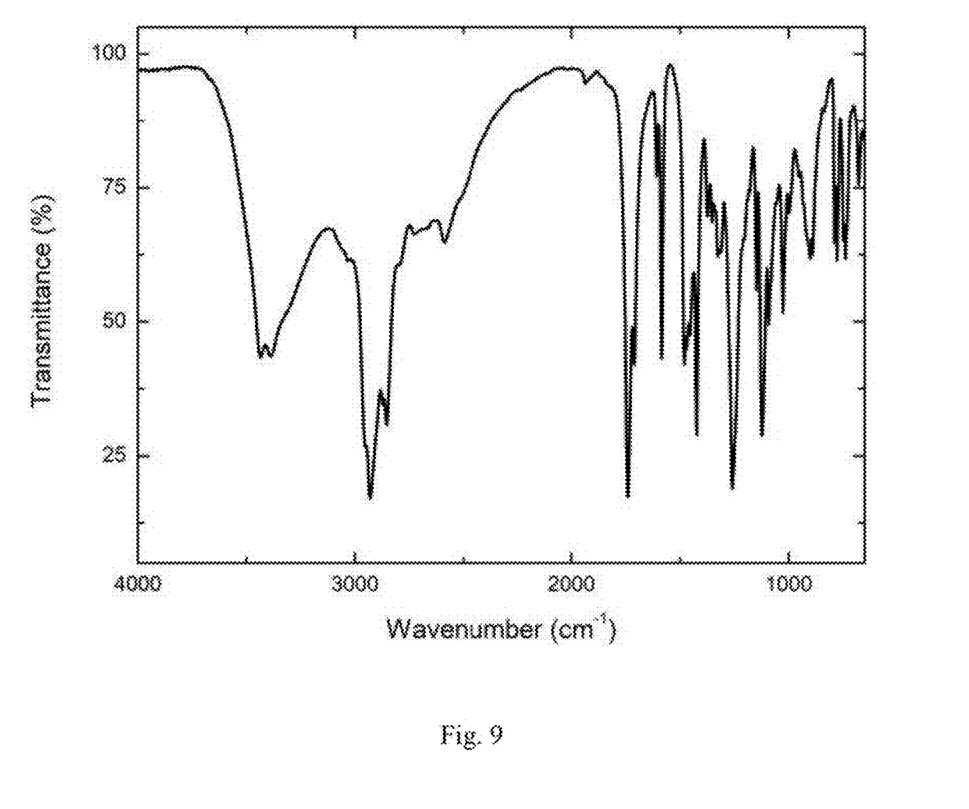
FIG. 9 shows a Fourier transform infrared (FTIR) spectrum of the crystalline Form I of anhydrous Treprostinil of the present invention.

In one embodiment, the present invention provides a crystalline Form I of anhydrous Treprostinil having a 1% KBr Fourier Transform infrared (FTIR) spectrum comprising peaks at 3435±4 $cm^{-1}$, 3389±4 $cm^{-1}$, 2930±4 $cm^{-1}$, 2872±4 $cm^{-1}$, 2854±4 $cm^{-1}$, 2727±4 $cm^{-1}$, 2588±4 $cm^{-1}$, 17404 $cm^{-1}$, 1711±4 $cm^{-1}$, 1608±4 $cm^{-1}$, 1585±4 $cm^{-1}$, 1480±4 $cm^{-1}$, 1469±4 $cm^{-1}$, 1455±4 $cm^{-1}$, 1424±4 $cm^{-1}$, 1374±4 $cm^{-1}$, 1352±4 $cm^{-1}$, 1326±4 $cm^{-1}$, 1312±4 $cm^{-1}$, 1259±4 $cm^{-1}$, 1148±4 $cm^{-1}$, 1122±4 $cm^{-1}$, 1092±4 $cm^{-1}$, 1026±4 $cm^{-1}$, 997±4 $cm^{-1}$, 952±4 $cm^{-1}$, 901±4 $cm^{-1}$, 890±4 $cm^{-1}$, 788±4 $cm^{-1}$, 777±4 $cm^{-1}$, 747±4 $cm^{-1}$, 738±4 $cm^{-1}$, and 677±4 $cm^{-1}$. In a preferred embodiment, the present invention provides a crystalline Form I of anhydrous Treprostinil having a 1% KBr FTIR spectrum substantially as shown in FIG. 9.

In one embodiment, the present invention provides a crystalline anhydrous Treprostinil containing less than about 0.05% Treprostinil ethyl ester and less than about 0.05% Treprostinil dimers. In a preferred embodiment, the crystalline anhydrous Treprostinil containing less than about 0.02% Treprostinil ethyl ester and less than about 0.02% Treprostinil dimers. More preferably, the crystalline anhydrous Treprostinil containing non-detectable amounts of Treprostinil ethyl ester and Treprostinil dimers.

In one embodiment, the present invention provides a crystalline anhydrous Treprostinil having a purity of at least 99.90%, preferably at least 99.95%, and most preferably at least 99.99% aside from the residual solvents and water.

Therefore, the crystalline Form I of anhydrous Treprostinil is a stable crystalline form, which can provide steady physicochemical properties for pharmaceutical formulations, and is advantageous widely and safety used in storage, shipment, and handling for commercially considerations.

EXAMPLES

X-ray Powder Diffraction (XRPD) Analysis: The XRPD patterns were collected on a Bruker D2 PHASER diffractometer with fixed divergence slits and 1D LYNXEYE detector. The samples (ca. 100 mg) were flatly placed on a sample holder. The prepared samples were analyzed over a 2θ range from 2° to 50° with step size of 0.02 degrees and step time of 1 second using $CuK_\alpha$ radiation at a power of 10 mA and 30 kV. The $CuK_\beta$ radiation was removed by a divergent beam nickel filter.

Differential Scanning Calorimetry (DSC) Analysis: The DSC thermogram patterns were collected on a TA DISCOVERY DSC25 instrument. The samples were weighed into an aluminum pan with a crimping closed aluminum lid. The prepared samples were analyzed from 25° C. to 200° C. at scan rate of 10° C./min under a flow of nitrogen (ca. 50 ml/min). The melting temperature and heat of fusion were calibrated by indium (In) before measurement.

Fourier Transform Infrared (FTIR) Analysis: The FTIR spectra were collected on a Perkin Elmer SPECTRUM 100 instrument. The samples were mixed with potassium bromide (KBr) in an approximately 1:100 ratio (w/w) using an agate mortar and pestle. The mixture was compressed in a pellet die at a pressure of about 10 to 13 tonnes for 2 minutes. The resulting disk was scanned 4 times versus a collected background from 4000 $cm^{-1}$ to 650 $cm^{-1}$ at a resolution of 4 $cm^{-1}$. The data was baseline corrected and normalized.

Ultra Performance Liquid Chromatography (UPLC) Analysis: The UPLC spectra were collected on a Waters ACQUITY UPLC instrument. The conditions were shown as the following: The sample is diluted to 1 mg/ml by 50l/50 (v/v) acetonitrile/$H_2O$. The column is Waters BEH $C_{18}$, 1.7 μm, 2.1*150 mm. The mobile phase is 60/40 (v/v) buffer/acetonitrile from 0 to 10 min, gradient changes of buffer/acetonitrile from 60/40 to 5/95 (v/v) (curve 6) from 10 to 20 min, 5/95 (v/v) buffer/acetonitrile from 20 to 25 min, gradient changes of buffer/acetonitrile from 5/95 to 0/100 (v/v) (curve 6) from 25 to 30 min, 0/100 (v/v) buffer/acetonitrile from 30 to 35 min. Buffer solution is pH 3.0 aqueous solution adjusted by trifluoroacetic acid. The flow rate is set as 0.42 ml/min. Column temperature is set as 45° C., sample temperature is set as 25° C. Injection is 1.5 μL. Run time is 35 min. UV detector is set as 210 nm.

Example 1

Stability of Treprostinil in Ethanol 1.00 g Treprostinil was dissolved in 5 ml ethanol in a glass vial at room temperature to form a homogenous solution, which was stirred at 40±1° C. oil bath and periodically sampled to UPLC measurement for tracing the formation of Treprostinil ethyl ester and Treprostinil dimers. The UPLC results were shown in the following Table 2. The Treprostinil ethyl ester was generated at a formation rate of about 0.2% per hour at 40±1° C., indicating that the carboxylic acid group (—COOH) of Treprostinil is active and can be easily esterified with alcohols. On the other hand, the Treprostinil dimers were also generated at a formation rate of about 0.01% per hour at 40±1° C., indicating that the active carboxylic acid group (—COOH) of Treprostinil can be easily intramolecularly esterified with the hydroxyl group (—OH) of Treprostinil.

TABLE 2

| Time (h) | Treprostinil | Treprostinil ethyl ester (IT201e2) | Treprostinil dimer-1 (IT201d1) | Treprostinil dimer-2 (IT201d2) |
|---|---|---|---|---|
| 0 | 99.88% | 0.02% | 0.04% | 0.06% |
| 2 | 99.50% | 0.39% | 0.04% | 0.07% |
| 4 | 99.07% | 0.81% | 0.06% | 0.06% |
| 6 | 98.68% | 1.18% | 0.07% | 0.07% |
| 8 | 98.15% | 1.64% | 0.10% | 0.11% |
| 10 | 97.73% | 2.04% | 0.12% | 0.11% |
| 12 | 97.41% | 2.37% | 0.13% | 0.09% |

Example 2

Stability of Treprostinil 0.01% g Treprostinil was placed in a glass vial and stirred at 40±1° C. oil bath and periodically sampled to UPLC measurement for tracing the formation of Treprostinil ethyl ester and Treprostinil dimers. The UPLC results were shown in the following Table 3. The Treprostinil dimers were generated at a formation rate of about 0.01% per hour at 40±1° C., indicating that the carboxylic acid group (—COOH) of Treprostinil is active and can be easily intramolecularly esterified with the hydroxyl group (—OH) of Treprostinil.

TABLE 3

| Time (h) | Treprostinil | Treprostinil ethyl ester (IT201e2) | Treprostinil dimer-1 (IT201d1) | Treprostinil dimer-2 (IT201d2) |
|---|---|---|---|---|
| 0 | 99.90% | ND* | 0.04% | 0.06% |
| 2 | 99.89% | ND* | 0.06% | 0.05% |
| 4 | 99.88% | ND* | 0.06% | 0.06% |
| 6 | 99.84% | ND* | 0.07% | 0.08% |
| 8 | 99.83% | ND* | 0.08% | 0.09% |
| 10 | 99.79% | ND* | 0.09% | 0.12% |
| 12 | 99.77% | ND* | 0.10% | 0.13% |

*ND means non-detectable.

Example 3

Filterability of Treprostinil Crystal

The filterability of sample solution is numerical estimated by the pressure changes inside the microfiltration assemblies during filtering. The microfiltration assemblies with 47 mm fritted glass, 0.22 μm hydrophilic PVDF filter membrane, 250 ml bottle, PANCHUM VP-900 dry pump, and an external pressure gauge were settled for tracing the pressure changes during filtration. The usage volume of sample solution for filtering was set as 100 ml and the filtering temperature was set as 25±1° C. for comparing the filterability of samples in a similar experimental condition.

Sample of crystalline Form I of anhydrous Treprostinil in ethyl acetate (containing 3% v/v water) was prepared from Example 5, and the concentration is about 0.05 g/ml. Sample of crystalline Form A of anhydrous Treprostinil in acetonitrile was prepared as disclosed by U.S. Pat. No. 9,278,903 Example 12, and the concentration is about 0.02 g/ml. Sample of monohydrated Treprostinil crystal in ethanol/water was prepared as disclosed by WO 2009/137066 Example 2, and the concentration is about 0.05 g/ml. The pressure changes of pure ethyl acetate, pure acetonitrile, crystalline Form I of anhydrous Treprostinil in ethyl acetate (containing 3% v/v water), crystalline Form A of anhydrous Treprostinil in acetonitrile, and monohydrated Treprostinil crystal in ethanol/water during filtration were measured and the results am shown in FIG. 10.

Figure 10:
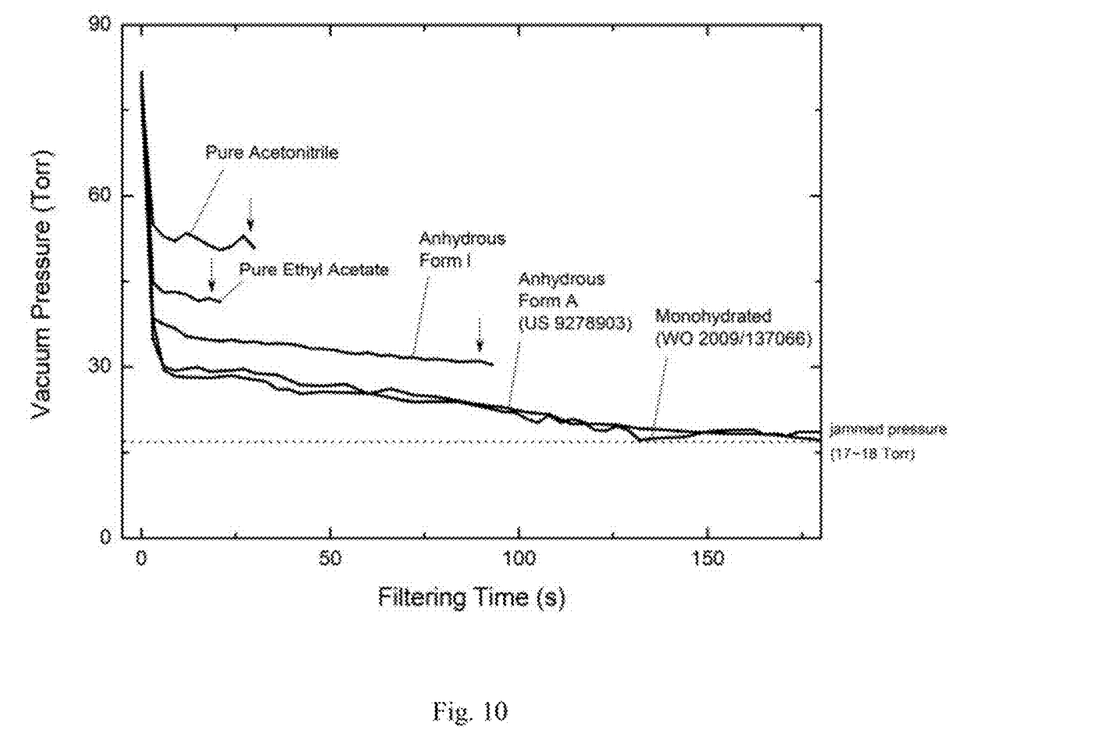
FIG. 10 shows the pressure changes of pure ethyl acetate, pure acetonitrile, the crystalline Form I of anhydrous Treprostinil in ethyl acetate (Anhydrous Form I), the crystalline Form A of anhydrous Treprostinil in acetonitrile (U.S. Pat. No. 9,278,903), and monohydrated Treprostinil crystal in ethanol/water (WO 2009/137066) during filtering.

As shown in FIG. 10, the pressure of pure ethyl acetate decreases quickly from about 80 torr to about 45 torr within about 3 seconds from the beginning of filtration, and then decreases smoothly from about 45 torr to about 41 torr (about 3 seconds to about 21 seconds) until all of the solvents were filtered out (arrow indicates the finish time of filtration at about 21 seconds). Comparing with the pressure change of crystalline Form I of anhydrous Treprostinil in ethyl acetate (containing 3% v/v water) during filtration, it decreases quickly from about 80 torr to about 39 torr within about 3 seconds from the beginning of filtration, and then decreases smoothly from about 39 torr to about 30 torr (about 3 seconds to about 92 seconds) until all of the solvents were filtered out (arrow indicates the finish time of filtration at about 92 seconds).

On the other hand, the pressure of pure acetonitrile decreases quickly from about 80 torr to about 53 torr within 3 seconds from the beginning of filtration, and then decreases smoothly from about 53 torr to about 51 torr (about 3 seconds to about 30 seconds) until all of the solvents were filtered out (arrow indicates the finish time of filtration at about 30 seconds). The result indicates that the filterability of pure acetonitrile is better than pure ethyl acetate. However, the pressure of crystalline Form A of anhydrous Treprostinil in acetonitrile decreases quickly from about 80 torr to about 30 torr within 3 seconds from the beginning of filtration, and then decreases smoothly from about 30 torr to about 18 torr (about 3 seconds to about 180 seconds). Until 180 seconds, there are still 20 to 30 ml solution residing on the microfiltration assemblies, and the filtration rate becomes very slow. The filterability change is result from the effect of crystal characteristics rather than solvent types. Comparing with these results, the filterability of crystalline Form I of anhydrous Treprostinil in ethyl acetate (containing 3% v/v water) is obviously much better (higher pressure and shorter filtration time) than the crystalline Form A of anhydrous Treprostinil in acetonitrile.

Besides, the pressure of monohydrated Treprostinil crystal in ethanol/water also decreases quickly from about 80 torr to about 30 torr within about 3 seconds from the beginning of filtration, and then decreases smoothly from about 30 torr to about 18 torr (about 3 seconds to about 180 seconds). Until 180 seconds, there are still about 20 to 30 ml solution residing on the microfiltration assemblies, and the filtration rate becomes very slow. It is obvious that the filterability of crystalline Form I of anhydrous Treprostinil in ethyl acetate (containing 3% v/v water) is much better (higher pressure and shorter filtering time) than the monohydrated Treprostinil crystal in ethanol/water.

For filtering the samples of crystalline Form A of anhydrous Treprostinil in acetonitrile and monohydrated Treprostinil crystal in ethanol/water, almost 80% of solution has been filtered until about 180 seconds. The residual solution (~20%) was jammed above the filter membrane without significant filtrate dripping. Therefore, the filter membrane area has to be substantially increased while filtering the crystalline Form A of anhydrous Treprostinil in acetonitrile or monohydrated Treprostinil crystal in ethanol/water in industry scale; otherwise, the industrial manufacturing processes of filtering them will face a big problem. In contrast, the crystalline Form I of anhydrous Treprostinil in ethyl acetate (containing 3% v/v water) with better filterability of the present invention can easily overcome the problem.

Example 4

Preparation of Crystalline Form I of Anhydrous Treprostinil

Crude Treprostinil (2.00 g) was dissolved in 120 ml ethyl acetate with 2% (v/v) water. Afterwards, the Treprostinil solution was concentrated under vacuum (about 10 Torr) at 20° C. until most Treprostinil crystals are precipitated. Thereafter, the resulting precipitate crystal was filtered and rinsed, and then dried under high vacuum (about 0.01 Torr) at 20° C. for 1 hour to give 1.62 g crystalline Form I of anhydrous Treprostinil. The XRPD, DSC, and FTIR results are the same as shown in FIG. 7, FIG. 8 and FIG. 9.

Example 5

Preparation of Crystalline Form I of Anhydrous Treprostinil 2-(((1R,2R,3aS,9aS)-2-hydroxy-1-((S)-3-hydroxyoctyl)-2,3,3a,4,9,9a-hexahydro-1H-cyclopenta[b]naphthalen-6-yl)oxy)acetonitrile (5.50 g, 14.8 mmol) was dissolved in 45 ml 2-propanol and followed by addition of 21 ml potassium hydroxide solution (16% w/v), and stirred at 80° C. for 2 hours. Afterwards, the reaction mixture was slowly cooled to the room temperature and added by hydrochloric acid solution to adjust the pH value to 10 to 12. The methanol was then removed by concentrating. The resulting solution was washed by ethyl acetate. The residual aqueous layer was acidified by adding acid to adjust the pH value to 2 to 3, and then extracted by 131 ml ethyl acetate. The extracted organic layers were washed with water. The Treprostinil solution (containing ethyl acetate and 3% (v/v) water) was concentrated under vacuum (about 10 Torr) at 20° C. until most Treprostinil crystals are precipitated. Thereafter, the resulting precipitate crystal was filtered and rinsed, and then dried under high vacuum (about 0.01 Torr) at 20° C. for 2 hours to give 4.79 g crystalline Form I of anhydrous Treprostinil. The XRPD, DSC, and FTIR results are the same as shown in FIG. 7, FIG. 8 and FIG. 9.

Example 6

Figure 11:
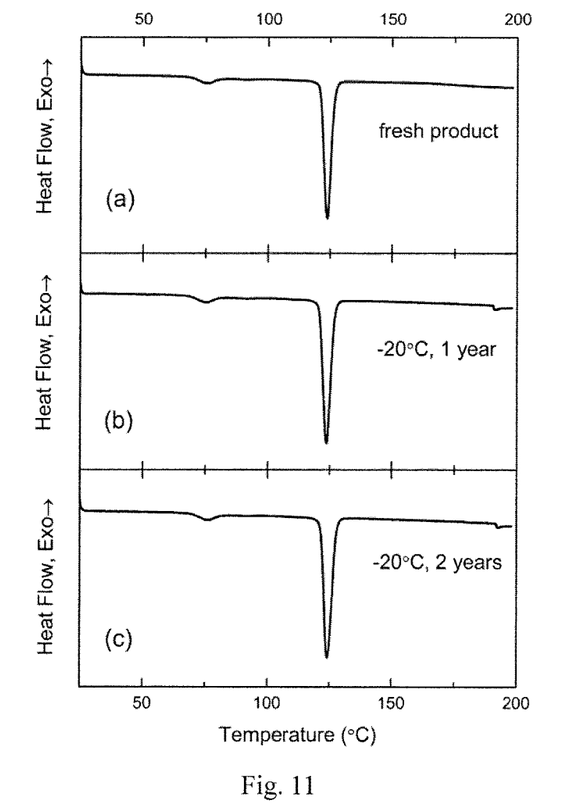
FIG. 11 shows the differential scanning calorimetry (DSC) thermogram patterns of the crystalline Form I of anhydrous Treprostinil of the present invention whiling keeping at −20° C. (a) when being a fresh product, (b) for one year, and (c) for two years.
Figure 12:
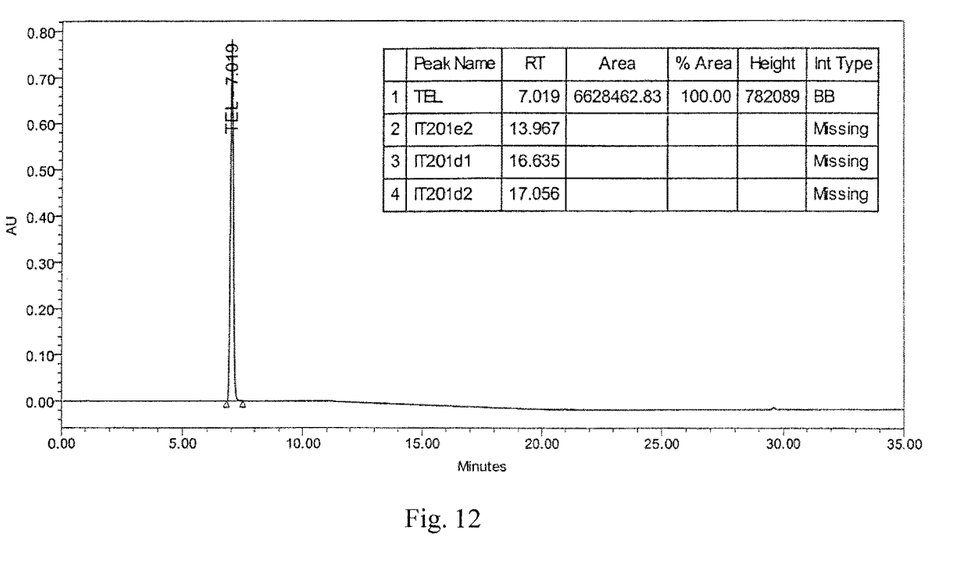
FIG. 12 shows the purity of the crystalline Form I of anhydrous Treprostinil of the present invention.

Preparation of Crystalline Form I of Anhydrous Treprostinil 2-(((1R,2R,3aS,9aS)-2-hydroxy-1-((S)-3-hydroxyoctyl)-2,3,3a,4,9,9a-hexahydro-1H-cyclopenta[b]naphthalen-6-yl)oxy)acetonitrile (340.0 g, 0.92 mol) was dissolved in 2.75 L 2-propanol and followed by addition of 1.35 L potassium hydroxide solution (16% w/v), and stirred at 80° C. for 2 hours. Afterwards, the reaction mixture was slowly cooled to the room temperature and added by hydrochloric acid solution to adjust the pH value to 10 to 12 The methanol was then removed by concentrating. The resulting solution was washed by ethyl acetate. The residual aqueous layer was acidified by adding acid to adjust the pH value to 2 to 3, and then extracted by 8 L ethyl acetate. The extracted organic layers were washed with water. The Treprostinil solution (containing ethyl acetate and 4.2% (v/v) water) was concentrated under vacuum (about 20 Torr) at 20° C. until most Treprostinil crystals are precipitated. Thereafter, the resulting precipitate crystal was filtered and rinsed, and then dried under high vacuum (about 0.05 Torr) at 20° C. for 18 hours to give 311.5 g crystalline Form I of anhydrous Treprostinil. The DSC results of fresh product sample and samples stored at −20° C. for one and two years are shown in FIG. 11. The purity of crystals was measured by UPLC, as shown in FIG. 12. As shown in FIG. 12, the Treprostinil ethyl ester (IT201e2), Treprostinil dimers (IT201d1 and IT201d2) are non-detectable, and the other impurities are not found. The purity of the crystalline Form I of anhydrous Treprostinil is ultrapure (100.00%).

It will be understood that particular embodiments described herein are shown byway of illustration and not as limitations of the invention. The principal features of this invention can be employed in various embodiments without departing from the scope of the invention. Those skilled in the art will recognize or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

All of the compounds and/or methods disclosed and claimed herein can be made and executed without undue experimentation in light of the present disclosure. While the compounds and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the an are deemed to be within the spirit, scope and concept of the invention as defined by the appended claims.

What is claimed is:

1. A crystalline Form I of anhydrous Treprostinil, having a X-ray powder diffraction (XRPD) pattern comprising a strongest characteristic peak at 3.1±0.2° and substantially free of characteristic peak at 6.5±0.2°; and having a differential scanning calorimetry (DSC) thermogram pattern comprising a strongest endothermic peak at 124±5° C. and substantially free of an endothermic peak at 95±5° C.

2. The crystalline Form I of anhydrous Treprostinil of claim 1, wherein said Form I is substantially free of any other form of crystalline treprostinil.

3. The crystalline Form I of anhydrous Treprostinil of claim 1, wherein the DSC thermogram pattern comprises the strongest endothermic peak having an enthalpy of greater than 60 J/g at 124±5° C., and another endothermic peak with an enthalpy of not more than 10 J/g at 60 to 80° C.

4. The crystalline Form I of anhydrous Treprostinil of claim 1, having a purity of at least 99.95% aside from residual solvents and water.

5. A crystalline anhydrous Treprostinil containing less than 0.05% Treprostinil ethyl ester and less than 0.05% Treprostinil dimers.

6. The crystalline anhydrous Treprostinil of claim 5, containing less than 0.02% Treprostinil ethyl ester and less than 0.02% Treprostinil dimers.

7. A method for preparing crystals of anhydrous Treprostinil containing less than 0.05% Treprostinil ethyl ester and less than 0.05% Treprostinil dimers, which comprises the steps of:
(a) providing a Treprostinil solution containing Treprostinil, an organic solvent selected from the group consisting of methyl acetate, ethyl acetate, isopropyl acetate, and mixtures thereof, and 1% to 8% (v/v) water;
(b) concentrating the Treprostinil solution under a pressure of 1 to 200 Torr at 30±15° C. until most crystals are precipitated;
(c) filtering out and optionally rinsing the crystals thereby isolating the crystals; and
(d) drying the crystals at 20±5° C.

8. The method according to claim 7, wherein the crystals of anhydrous Treprostinil are crystalline Form I of anhydrous Treprostinil having a X-ray powder diffraction (XRPD) pattern comprising a strongest characteristic peak at 3.1±0.2° and substantially free of characteristic peak at 6.5±0.2°; and having a differential scanning calorimetry (DSC) thermogram pattern comprising a strongest endothermic peak at 124±5° C. and substantially free of an endothermic peak at 95±5° C.

9. A crystalline Form I of anhydrous Treprostinil prepared by the method of claim 8.

10. The method according to claim 8, wherein said Form I is substantially free of any other form of crystalline Treprostinil.

11. The method according to claim 8, wherein the crystalline Form I has a DSC thermogram pattern comprising a strongest endothermic peak having an enthalpy of greater than 60 J/g at 124±5° C., and another endothermic peak with an enthalpy of not more than 10 J/g at 60 to 80° C.

12. The method according to claim 8, wherein the crystalline Form I has a purity of at least 99.95% aside from residual solvents and water.

13. The method according to claim 7, wherein the filtered crystals isolated in step (c) have a water content of less than 2%.

14. The method according to claim 7, wherein the filtered crystals isolated in step (c) do not comprise Treprostinil monohydrate.

15. The method according to claim 14, wherein the method consists essentially of steps (a) (d).

16. The method according to claim 7, wherein the Treprostinil crystals precipitated from the Treprostinil solution comprising the organic solvent and the water are more filterable than anhydrous Treprostinil crystals precipitated from an anhydrous aprotic solvent.

\* \* \* \* \*